United States Patent [19]

Broadhurst

[11] Patent Number: 4,994,473
[45] Date of Patent: Feb. 19, 1991

[54] PYRIDYL CONTAINING INSECTICIDES

[75] Inventor: Michael D. Broadhurst, Novato, Calif.

[73] Assignee: ICI Americas Inc., Wilmington, Del.

[21] Appl. No.: 263,604

[22] Filed: Oct. 31, 1988

Related U.S. Application Data

[63] Continuation-in-part of Ser. No. 121,839, Nov. 17, 1987, abandoned.

[51] Int. Cl.$^5$ .................... A61K 31/44; C07D 213/74
[52] U.S. Cl. .................... 514/335; 514/336; 514/346; 514/348; 514/349; 514/352; 514/353; 546/261; 546/283; 546/292; 546/296; 546/297; 546/305; 546/306; 546/310; 546/312
[58] Field of Search ............... 546/312, 310, 306, 305, 546/297, 296, 261, 283, 292; 514/335, 336, 346, 348, 349, 352, 353

[56] References Cited

U.S. PATENT DOCUMENTS

| | | | |
|---|---|---|---|
| 3,832,351 | 8/1974 | Tanaka et al. | 546/312 |
| 3,899,582 | 8/1975 | Tanaka et al. | 546/310 |
| 4,355,035 | 10/1982 | Haken et al. | 546/312 |
| 4,628,100 | 12/1986 | Lo | 546/296 |
| 4,767,771 | 8/1988 | Baker et al. | 546/312 |

FOREIGN PATENT DOCUMENTS 207000 12/1986 European Pat. Off. .
50-94133 7/1975 Japan .
1192995 5/1970 United Kingdom .

OTHER PUBLICATIONS

Tanaka et al., Agricultural & Biological Chemistry, vol. 41, pp. 1953–1959 (1977).

Primary Examiner—Bernard I. Dentz
Attorney, Agent, or Firm—Joel G. Ackerman

[57] ABSTRACT

Insecticides of the general formula

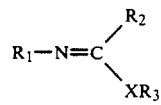

wherein $R_1$ is an optionally substituted 5- to 10-member heterocyclic moiety; $R_2$ is an optionally substituted alkyl, cycloalkyl or alkenyl moiety; X is oxygen, sulfur or —NH—; and $R_3$ is: (a) an optionally substituted 3-phenoxyphenalkyl, 3-phenoxypyridylalkyl, 3-(pyridyloxy)phenalkyl, 3-phenylaminophenoalkyl, 3-benzylphenalkyl or 3-benzyloxyphenalkyl moiety; (b) a benzylfuranylmethyl moiety; (c) a 3- or 4-substituted benzyl or tetrafluorobenzyl moiety; (d) 4-phenoxy-2-butyn-2-yl; or (e) 2-methyl-3-phenylbenzyl.

45 Claims, No Drawings

PYRIDYL CONTAINING INSECTICIDES

CROSS-REFERENCE TO RELATED APPLICATIONS

This application is a continuation-in-part of application Ser. No. 121,839 filed Nov. 17, 1987 and now abandoned.

This invention relates to a series of insecticidal heterocyclic compounds having the general formula

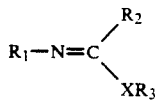  (I)

wherein $R_1$ is an optionally substituted 5- to 10-member heterocyclic moiety;

$R_2$ is an optionally substituted alkyl, cycloalkyl or alkenyl moiety;

X is oxygen, sulfur or —NH—; and $R_3$ is: (a) an optionally substituted 3-phenoxyphenalkyl, 3-phenoxypyridylalkyl, 3-(pyridyloxy)phenalkyl, 3-phenylaminophenalkyl, 3-benzylphenalkyl or 3-benzyloxyphenalkyl moiety; (b) a benzylfuranylmethyl moiety; (c) a 3- or 4-substituted benzyl or tetrafluorobenzyl moiety; (d) 4-phenoxy-2-butyn-2-yl; or (e) 2-methyl-3-phenylbenzyl.

More specifically, $R_1$ is a heterocyclic moiety selected from pyridyl, quinolyl, isoquinolyl, oxazolyl, isoxazolyl, thiazolyl, isothiazolyl, thiadiazolyl, furanyl, pyrazolyl, or benzoxazolyl or benzothiazolyl bonded to the imidate/amidine nitrogen atom through an aromatic carbon atom, said heterocyclic moiety being optionally substituted by from 1 to 4 groups selected from halo, $C_1-C_6$ alkyl, $C_1-C_4$ haloalkyl, $C_1-C_4$ haloalkoxy, $C_1-C_4$ alkoxy, $C_1-C_4$ alkylthio, methoxycarbonyl, or phenyl, provided that $R_1$ is not 3-chloro-5-trifluoromethylpyrid-2 yl;

$R_2$ is methyl, ethyl, n-propyl, $C_3-C_7$ branched alkyl, $C_3-C_4$ cycloalkyl, $C_2-C_6$ alkenyl, $C_2-C_6$ haloalkenyl, $C_1-C_6$ haloalkyl, $C_2-C_6$ alkoxyalkyl or cyclopropyl substituted by up to four methyl groups or up to two halogens;

X is oxygen, sulfur or —NH—;

when X is oxygen, then $R_3$ is:

(a) 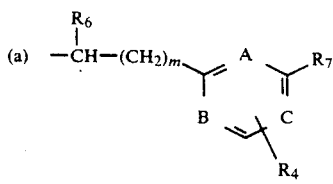

in which m is 0 or 1;

A, B and C are each carbon or nitrogen, provided that A, B and C are not all nitrogen and if two of A, B and C are nitrogen, then A and C are nitrogen;

$R_4$ is hydrogen, monohalo or dihalo;

$R_6$ is hydrogen, methyl, fluoro or ethynyl; and $R_7$ is

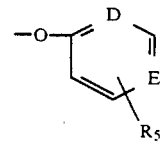

in which D and E are each carbon or nitrogen provided that both D and E are not nitrogen, and further provided that if any of A, B or C is nitrogen, then D and E are both carbon; and $R_5$ is hydrogen, $C_1-C_4$ alkyl, $C_1-C_4$ alkoxy, trifluoromethyl, cyano, $C_1-C_4$ alkylthio, $C_1-C_4$ alkylsulfonyl, or mono- or polyhalo;

(ii) 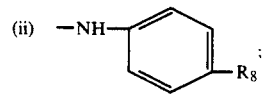

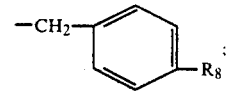

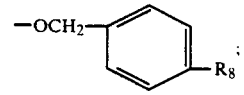

in which $R_8$ is hydrogen or halogen; or (iii) —O—CH$_2$—CH=CH$_2$;

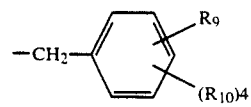 (b)

in which (i) $R_9$ is 4-fluoro, 4methoxymethyl, or 4and $R_{10}$ is fluoro or (ii) $R_9$ is 3- or 4-allyl, 3- or 4-propargyl, or 3- or 4-(mono-or dihalo)allyl, and $R_{10}$ is hydrogen or fluoro;

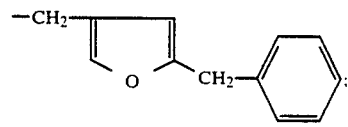 (c)

(d) 4-phenoxy-2-butyn-2-yl;
(e) 3-bromo-4-fluorobenzyl;
(f) 4-(benzyloxy)benzyl;
(g) 4-(4-fluorobenzyloxy)benzyl; or (h) 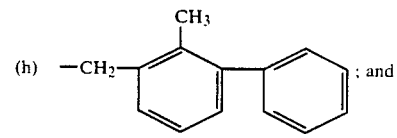 ; and when X is sulfur or —NH—, then $R_3$ is (j) 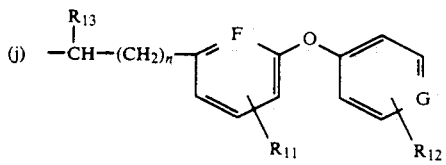

in which n is 0 or 1; F and G are independently nitrogen or carbon, provided that F and G are not both nitrogen; $R_{11}$ is hydrogen or halo; $R_{12}$ is hydrogen, mono- or di-halo, $C_1$-$C_4$ alkyl, $C_1$-$C_4$ alkoxy, trifluoromethyl, cyano, $C_1$-$C_4$ alkylthio, $C_1$-$C_4$ alkylsulfonyl; and $R_{13}$ is hydrogen or methyl; (k) pentafluorobenzyl; or (l) 2-methyl-3-phenylbenzyl.

The compounds of this invention demonstrate activity in controlling various types of insects, particularly in foliar application.

Another aspect of this invention involves insecticidal compositions comprising an insecticidally effective amount of a compound of the invention with an insecticidally suitable diluent or carrier.

In another aspect, this invention involves a method for controlling insects by administration of insecticidally effective amounts of the compounds or compositions of this invention to a locus where control is desired.

The term "insects" as used herein refers to the broad and commonly understood usage rather than to those creatures which in the strict biological sense are classified as insects. In addition to those belonging to the class Insecta, this term may include some classes of acarids such as mites and the like.

DETAILED DESCRIPTION OF THE INVENTION

The novel compounds of this invention have the general formula

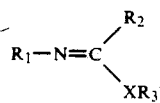

in which $R_1$, $R_2$, $R_3$ and X are as defined above. The term "imidate/amidine nitrogen atom" will be used to refer to the nitrogen atom shown in this general formula.

As used herein:

"halo" includes chloro, bromo, fluoro and iodo;

"alkyl" refers to saturated acyclic hydrocarbyl groups (straight or branched chain) having the indicated number of carbon atoms, e.g., methyl, ethyl, n-propyl, isopropyl, etc.;

"haloalkyl" and "haloalkoxy" refer to alkyl and alkoxy groups of the indicated number of carbon atoms substituted by one or more of the same or different halogen atoms;

"cycloalkyl" refers to saturated cyclic hydrocarbyl groups having the indicated number of carbon atoms, e.g., cyclopropyl, cyclobutyl, cyclopentyl and cyclohexyl;

"alkenyl" refers to unsaturated acyclic hydrocarbyl groups having the indicated number of carbon atoms and including one or more olefinic bonds, e.g., vinyl, propenyl, isopropenyl, 1-butenyl, butadienyl, and the like; and "alkoxyalkyl" refers to saturated acyclic moieties having two alkyl groups linked by an oxygen atom, with the total number of carbon atoms indicated, e.g., methoxymethyl, methoxyethyl, ethoxymethyl and the like;

"phenalkyl" refers to an alkyl group having from 1 to 4 carbon atoms substituted by a phenyl group, such as benzyl, phenethyl, and the like;

"propargyl" refers to the 2-propynyl group, —CH2-C≡CH; and

"allyl" refers to the 2-propenyl group —CH2—CH=CH2.

In general, $R_1$ is a 5- to 10member heterocyclic moiety, containing 1 or 2 rings, optionally substituted as described below. The heterocyclic groups represented by $R_1$, except for benzoxazolyl and benzothiazolyl, may be bonded to the imidate/amidine nitrogen atom at any position on the ring. The pyridyl groups thus include 2-, 3- and 4-pyridyl. The benzoxazolyl and benzothiazolyl groups have the formula

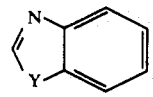

in which Y is oxygen or sulfur, respectively. In the compounds of this invention, these moieties are bonded to the imidate/amidine nitrogen atom through a carbon atom in the "aromatic" portion of the ring, that is, at the 4-, 5-, 6- or 7- position.

The heterocyclic ring represented by $R_1$ may be unsubstituted or may be substituted at any position by one or more halo, alkyl, alkoxy, haloalkyl, alkylthio, haloalkoxy, alkylsulfonyl, carbomethoxy, or phenyl groups, or by a combination of such groups. Preferred substituted rings include:

mono- and disubstituted pyridyl in which the substituents are halo, trifluoromethyl, methoxy, ethoxy, 2,2,2-trifluoroethoxy, methylthio, and/or methyl, except 3-chloro-5-trifluoromethyl-pyrid-2-yl;

mono-substituted oxazolyl, thiazolyl and thiadiazolyl rings in which the substituent is halo, methyl or trifluoromethyl; and 2-($C_1$-$C_4$ alkyl) benzoxazolyl and benzothiazolyl.

For the various subgroups falling within the general definition of $R_3$, preferred types are:

For $R_4$ and $R_{12}$: hydrogen and 2-,4- or 6-monohalo, particularly monochloro or monofluoro;

For $R_5$ and $R_{13}$: 2-, 3- or 4-halo, 2,4-, 3,4- or 3,5-dihalo, particularly difluoro, pentahalo, particularly pentafluoro, 4-methyl, 4-trifluoromethyl, 4methoxy, 4methylthio and 4methylsulfonyl.

The following are examples of specific embodiments of groups falling within the definition of $R_3$. For convenience in specifying positions of substitution of compounds of the type

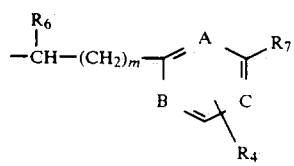

the position of attachment of the group

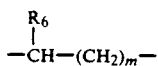

was given the number 1 and the position of attachment of group R7, the number 3. When A, B or C was a nitrogen atom, the compounds were designated pyrid-2-yl, pyrid-6-yl or pyrid-4-yl, respectively.

3-phenoxybenzyl,
3-phenoxy-(alpha-methyl)benzyl,
3-phenoxyphenethyl,
3-(4-pyridyloxy)benzyl,
4-pyridyloxybenzyl,
3-(4-fluorophenoxy)benzyl,
3-(4-chlorophenoxy)benzyl,
3-(4-bromophenoxy)benzyl,
3-(4-iodophenoxy)benzyl,
3-(2,4-difluorophenoxy)benzyl,
3-(3,4-difluorophenoxy)benzyl,
3-(3,5-difluorophenoxy)benzyl,
3-(2,3,4,5,6-pentafluorophenoxy)benzyl,
3-(4-fluorophenoxy)-4-fluorobenzyl,
3-(4-fluorophenoxy)-4-chlorobenzyl,
3-(4-chlorophenoxy)-4-fluorobenzyl,
3-phenoxy-4-fluorobenzyl,
3-(4-fluorophenoxy)-6-chlorobenzyl,
3-(4-fluorophenoxy)-5-fluorobenzyl,
3-(4-fluorophenoxy)-4,6-difluorobenzyl,
3-(4-methylphenoxy)benzyl,
3-(4-methoxyphenoxy)benzyl,
3-(3,4-difluorophenoxy)-4-fluorobenzyl,
3-(3-fluorophenoxy)benzyl,
3-(2-fluorophenoxy)benzyl,
3-(3-chlorophenoxy)benzyl,
3-(4-trifluoromethylphenoxy)benzyl,
3-(4-methylthiophenoxy)benzyl,
3-(4-fluorophenoxy)-(alpha-fluoro)benzyl,
3-phenoxy-pyrid-2-yl methyl,
3-phenoxy-pyrid-4-yl methyl,
3-phenoxy-pyrid-6-yl methyl,
3-(4-methylphenoxy)pyrid-2-ylmethyl,
3-(4-fluorophenoxy)pyrid-2-ylmethyl,
3-(4-chlorophenoxy)pyrid-2-ylmethyl,
3-(4-fluorophenoxy)pyrid-4-ylmethyl,
3-(4-bromophenoxy)pyrid-2-ylmethyl,
3-(4-chlorophenoxy)pyrid-4-ylmethyl,
3-(4-chlorophenoxy)pyrid-6-ylmethyl,
3-(3,4-difluorophenoxy)pyrid-2-ylmethyl,
3-(pyrid-2-yloxy)benzyl,
3-(4-chloropyrid-2 yloxy)benzyl,
2,3,4,5,6-tetrafluorobenzyl,
4-methoxymethyl-2,3,5,6-tetrafluorobenzyl,
4-propargyl-2,3,5,6-tetrafluorobenzyl,
3-allyloxybenzyl,
1 3-phenoxyphenyl)prop-2-ynyl,
3-(benzyl)benzyl,
3-(benzyloxy)benzyl,
3-(4-fluorobenzyloxy)benzyl,
3-(phenylamino)benzyl,
3-(4-fluorophenylamino)benzyl,
2-methyl-3-phenylbenzyl,
3-bromo-4-fluorobenzyl,
4-phenoxy-2-butyn-2-yl,
4-(4-fluorobenzyloxy)benzyl,
5-benzyl-3-furanylmethyl.

The compounds of this invention may be prepared by the following processes in which $R_1$, $R_2$, $R_3$ and X are as previously defined.

Products of type (I) in which X is oxygen are prepared by reaction of an imidoyl chloride with an alkali metal alkoxide according to the general reaction (A)

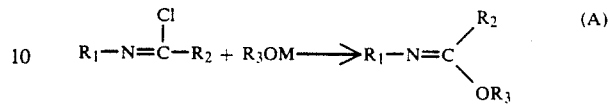

in which M is an alkali metal, preferably sodium or potassium.

This reaction is conducted at a temperature of from about $-70°$ C. to about $+65°$ C., most preferably at about room temperature, for a time which may range from about 5 minutes up to about 48 hours. The reaction is conducted in the presence of a solvent, for example, an aromatic hydrocarbon such as benzene, toluene, xylene or naphthalene, or an ether, such as diethyl ether, diisopropyl ether, diisoamyl ether, dibutyl ether, furan, 1,2-dimethoxyethane, or tetrahydrofuran (preferably tetrahydrofuran). In some instances, apparent to those skilled in the art, it is advantageous to add the solution of the alkali metal alkoxide to a solution of the imidoyl chloride or to use substantial excesses of alkoxide. The resulting product may be recovered by conventional techniques.

The alkoxide $R_3OM$ is produced by reaction of an appropriate alcohol, such as 3-phenoxybenzyl alcohol, with an alkali metal-containing base, for instance, an alkali metal hydride (e.g., potassium or preferably sodium hydride) in the presence of a solvent such as that used in reaction of the alkali metal alkoxide with the imidoyl chloride. In general, this reaction is conducted at reflux temperature under an inert atmosphere for a time which may range up to about 2 hours.

Some compounds of this invention are produced from alcohols ($R_3OH$) which are sensitive to, and could be adversely affected (e.g. decomposed) by, strong bases such as the alkali metal-containing bases (e.g. alkali metal hydrides) used to prepare the alkoxides ($R_3OM$). Alcohols which may be sensitive to such strong bases include phenoxypyridyl alkanols, alpha-ethynyl alcohols ($R_6$ is ethynyl) such as 1-(3-phenoxyphenyl)-2-propyn-1-ol and tetrafluoropropargylbenzyl alcohol.

Compounds of this type may be made by direct reaction of the alcohol with the imidoyl chloride in the presence of a tertiary amine base and a reaction-promoting amount of a 4-(di-lower alkyl)aminopyridine, preferably 4-dimethylaminopyridine.

Tertiary amines which may be used in this process include trialkylamines such as trimethyl-, triethyl-, tri-n-butyl-amine and the like, including tertiary amines having mixed alkyl groups, N,N-dialkylanilines such as N,N-dimethylaniline, pyridine and various substituted pyridines.

Preferred tertiary amines, primarily for economic reasons, are triethylamine, N,N-dimethylaniline, and pyridine. The tertiary amine may even be an additional amount of the promoter 4(di-lower alkyl)aminopyridine, over and above that amount needed for promoting the reaction.

The tertiary amine is preferably used in a stoichiometric amount with respect to the alcohol, but may be used in excess of that amount. The promoter 4-(di-lower alkyl)aminopyridine may be used in an amount from about 0.05 to about 1 equivalent per equivalent of alcohol, preferably from about 0.05 to about 0.15 equivalent per equivalent, most preferably about 0.1.

This process is preferably conducted at temperatures of from about 20° C. to about 50° C. Lower temperatures may be used, but the reaction rate would be much slower. The process is carried out in the presence of an inert solvent such as an aromatic hydrocarbon (for instance, benzene, toluene or xylene), a chlorinated solvent (such as methylene chloride, ethylene dichloride or chlorobenzene) or an ether (such as diethyl ether, dioxane or tetrahydrofuran).

While this process is particularly suitable for producing compounds from base-sensitive alcohols, it may be used to produce compounds of this invention in general from other alcohols as described.

The alcohols, if not commercially available, can be prepared according to known methods such as those described in U.S. Pat. Nos. 4,256,893; 4,261,920 and 4,329,518, and Volumn 7 of the text "Chemie der Pflanzenschutz und Schadlingsbekampfungsmittel" (for phenoxybenzl, phenoxypyridyl and pyridyloxybenzl type alcohols); in the article by Elliott et al. *J. Chem. Soc.* (C), 1971, pp 2251-2554 (for S-benzyl-2-furanylmethanol); *Pesticide Science* 14, 56014 570 (1983) (for 2-methyl-3-phenylbenzyl alcohol); U.S. Pat. Nos. 4,370,346 and 4,594,355; British patent No. 2,122,616; European patent applications Nos. 196,156 and 271,240; and *J. Sci. Food & Agriculture* 18, 167 (1967) for various substituted benzyl alcohols; European patent application No. 211,561 for 3-phenylaminobenzyl alcohols; Swiss patent No. 549,342 for 4-phenoxy-2-butyl-1-ol; and Japanese patent No. 49-27331 for 1-(3-phenoxyphenyl)-2-propyn-1-ol.

Alpha-fluorophenoxybenzyl compounds are made from the alphafluorobenzyl halide (preferably bromide) rather than the alcohol by reaction with an amide $R_1NHCOR_2$ in the presence of a halide ion binding agent such as silver oxide or a silver salt and an inert solvent. Reaction temperatures are from about $-20°$ C. to about 100° C.

The imidoyl chloride may be prepared from a starting amine having the formula $R_1NH_2$ or amide having the formula

$R_1NHCR_2$, depending on availability. The amines are either generally available or may be prepared by procedures known in the art, for example, those described in "Compendium of Organic Synthetic Methods", Harrison et al. (Wiley-Interscience, New York, 1971).

The amides, if not available, may be produced by reaction of the amine with an appropriate acid chloride having the formula

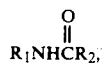
$R_2CCl$

The temperature of this reaction ranges from about $-40°$ C. to about $+80°$ C. Suitable solvents include hydrocarbon solvents such as toluene and chlorinated hydrocarbon solvents such as methylene chloride, chloroform, carbon tetrachloride, ethylene dichloride, tetrachloroethane and the like, preferably methylene chloride. This reaction is conducted in the presence of a base, preferably a tertiary amine. Suitable bases include triethylamine, quinoline, dimethylaniline, diethylaniline, and pyridine. Triethylamine is the preferred base. The resulting amide is recovered and purified by conventional means.

The imidoyl chloride may be prepared from the amide by reacting it with a chlorinating agent such as phosphorus pentachloride or phosgene in an organic solvent such as that utilized in the amide production (preferably methylene chloride). The reaction is carried out under an inert atmosphere for a time which may range up to 10 hours, preferably from 1 to 4 hours, at a temperature of from about 0° C. to about 110° C.

Before the imidoyl chloride-containing product is passed to the final step, all substances, such as phosphorus oxychloride or hydrogen chloride, which can react with the alkoxide, mercaptide, mercaptan or amine in the final step, should be removed. This can generally be accomplished by evaporation or distillation.

Compounds in which X is sulfur may be prepared similarly to those in which X is oxygen (by formation of the alkali metal mercaptide). Alternatively, they may be prepared by reaction of the corresponding imidoyl chloride with the appropriate mercaptan in the presence of a base according to the reaction

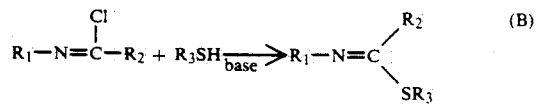
(B)

This process is carried out under reflux for a time of between about 30 and about 60 minutes. The base utilized is a tertiary amine such as that employed for production of the amide from the amine and is preferably triethylamine. This reaction is conducted in the presence of a suitable solvent such as that utilized in the reaction of an alkali metal alkoxide with the imidoyl chloride, and is preferably tetrahydrofuran. The reaction between the mercaptan and the imidoyl chloride is exothermic; consequently the addition of imidoyl chloride should be carefully controlled. The product may be recovered by conventional techniques.

Mercaptans of the formula $R_3SH$ are described in German Patent Application No. 2,944,849.

Compounds in which X is sulfur may also be prepared by alkylation of a thioamide according to the reaction:

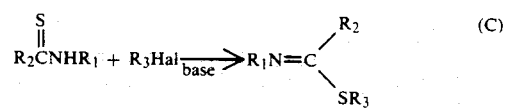
(C)

in which $R_1$, $R_2$ and $R_3$ are as defined above, and Hal stands for halo preferably chloro.

The thioamides, if not readily available, may be produced by reaction of the corresponding amine and Lawesson's Reagent. Reaction (C) is generally conducted at a temperature of from about $-20°$ to about 110° C., for a time of from about 1 to about 20 hours, in the presence of a solvent, for instance an aromatic hydrocarbon such as benzene, toluene, xylene or naphthalene or an ether such as diethyl, diisopropyl, diisoamyl or dibutyl ether, furan, tetrahydrofuran, or 1,2-dimethoxyethane, and an appropriate base such as an alkali metal hydride. The final product may be recovered by conventional techniques.

Compounds in which X is nitrogen may be produced by reaction of the appropriate imidoyl chloride with an amine according to the reaction

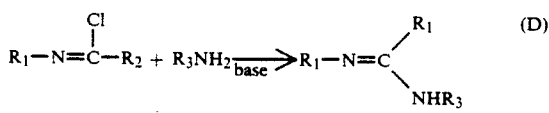

Again, a suitable solvent is tetrahydrofuran. This reaction may take up to 48 hours to complete and is conducted under an inert atmosphere at temperatures of −40 to +80° C. Again, the imidoyl chloride should be added in a controlled manner in order to maintain the temperature within the appropriate range. The starting amines are described for instance in European Patent Applications Nos. 6155 and 6180. The base is a tertiary amine, preferably triethylamine. The resulting product is recovered by conventional techniques.

The following represents an example of the preparation of compounds of this invention.

EXAMPLE

This example illustrates the general procedure for the preparation of compounds of this invention according to Reaction (A).

Preparation of N-(6-Chloro-3-pyridyl)-0-(3-phenoxybenzyl)isobutyrylimidate (Compound 1)

A. Preparation of the Amide

To a stirred solution of 10 grams (g) (0.078 mol) 5-amino-2-chloropyridine, and triethylamine (11.2 ml, 0.08 mol) in 100 x1 of dichloromethane was added 7.8 x1 (0.075 mol) of isobutyryl chloride dropwise chloromethane was added 7.8 ml (0.075 mol) of isobutyryl chloride dropwise with cooling in an ice bath. Following the addition, the ice bath was removed and when the reaction mixture reached room temperature, 100 ml of water was added. The layers were separated and the organic layer was dried over anhydrous sodium sulfate. Rotary evaporation provided 6-chloro-3-pyridylisobutyrylamide. The crude solid could be recrystallized from toluene to provide crystals, m.p. 118–120° C.

B. Preparation of the Imidoyl Chloride

To a stirred solution of the product of step (A) (2.0 g, 0.010 mol) in 50 ml of dichloromethane under an argon atmosphere was added phosphorus pentachloride (2.1 g, 0.010 mol). After 2 hours, the resulting solution was transferred to a rotary evaporator. The solvent was removed at 20 mmHg and the residue was evaporated at 40° under a vacuum of less than 1 mm Hg. The resultant N-(6-chloro-3-pyridyl)-1-chloro-2-methylpropylidene amine as a viscous oil, was immediately carried on to Step D.

C. Preparation of the Alkoxide

To a stirred suspension of sodium hydride (0.29 g, 0.012 mol) in 40 x1 of dry tetrahydrofuran (THF) under argon was added 2.2 g (0.011 mol) of 3-phenoxybenzyl alcohol. The resulting mixture was heated to reflux for 30 minutes and cooled. The resulting pale yellow solution of sodium 3-phenoxybenzylate was used in the final Step D.

D. Preparation of the Imidate

Crude imidoyl chloride from step (B) was dissolved in 10 ml of dry THF and added dropwise to the THF solution of alkoxide from step (C) with cooling at room temperature for several minutes. After an additional hour, the resulting product mixture was poured into hexane. It was then filtered through a pad of 25 g of silica gel. Rotary evaporation resulted in 2.9 g (76%) of a white solid, shown to be N-(6-chloro-3-pyridyl)-0-(3-phenoxybenzyl)isobutyrylimidate (I), m.p. 69°–77° C.

Table I shows representative compounds of this invention prepared according to the procedures described above.

TABLE I

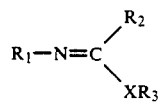

| Cmpd. No. | X | $R_1$ | $R_2$ | $R_3$ | Physical Constant |
|---|---|---|---|---|---|
| 1 | O | 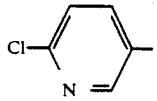 6-Cl-pyridyl | isopropyl | 3-phenoxybenzyl | m.p. 69–77° C. |
| 2 | O | 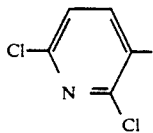 Cl-pyridyl-Cl | isopropyl | 3-phenoxybenzyl | oil |
| 3 | O | 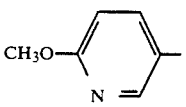 CH₃O-pyridyl | isopropyl | 3-phenoxybenzyl | oil |

TABLE I-continued $$R_1-N=C\begin{smallmatrix}R_2\\XR_3\end{smallmatrix}$$

| Cmpd. No. | X | R$_1$ | R$_2$ | R$_3$ | Physical Constant |
|---|---|---|---|---|---|
| 4 | O | 5-CF$_3$-pyridin-2-yl | isopropyl | 3-phenoxybenzyl | m.p. 50–55° C. |
| 5 | O | 6-F-pyridin-3-yl | isopropyl | 3-phenoxybenzyl | oil |
| 6 | O | 2,3,5-trifluoropyridin-6-yl | isopropyl | 3-phenoxybenzyl | oil |
| 7 | O | 6-Cl-pyridin-3-yl | cyclopropyl | 3-phenoxybenzyl | oil |
| 8 | O | 3,5-dimethylisoxazol-4-yl | isopropyl | 3-phenoxybenzyl | oil |
| 9 | O | 3-CF$_3$-5-isopropyl-1,2,4-thiadiazol | 2-chloro-2-methylpropyl (—C(CH$_3$)$_2$Cl) | 3-phenoxybenzyl | oil |
| 10 | O | 6-CH$_3$-pyridin-3-yl | isopropyl | 3-phenoxybenzyl | oil |
| 11 | O | 6-Br-pyridin-3-yl | isopropyl | 3-phenoxybenzyl | oil |
| 12 | O | 6-Br-pyridin-3-yl | —C(CH$_3$)$_2$Cl | 3-phenoxybenzyl | oil |
| 13 | O | 5-Br-pyridin-3-yl | isopropyl | 3-phenoxybenzyl | oil |
| 14 | O | 5-(methoxycarbonyl)furan-2-yl | isopropyl | 3-phenoxybenzyl | oil |

TABLE I-continued

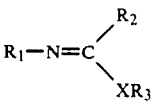

| Cmpd. No. | X | R₁ | R₂ | R₃ | Physical Constant |
|---|---|---|---|---|---|
| 15 | O | 2-methoxypyridin-5-yl (CH₃O-pyridine) | cyclopropyl | 3-phenoxybenzyl | oil |
| 16 | O | quinolin-6-yl | isopropyl | 3-phenoxybenzyl | oil |
| 17 | O | quinolin-3-yl | isopropyl | 3-phenoxybenzyl | oil |
| 18 | O | benzoxazol-6-yl | isopropyl | 3-phenoxybenzyl | oil |
| 19 | O | benzoxazol-5-yl | isopropyl | 3-phenoxybenzyl | oil |
| 20 | O | benzothiazol-6-yl | isopropyl | 3-phenoxybenzyl | oil |
| 21 | O | 2-isopropylbenzothiazol-6-yl | isopropyl | 3-phenoxybenzyl | oil |
| 22 | O | 2-chloropyridin-5-yl | isopropyl | 3-(4-fluorophenoxy)benzyl | oil |
| 23 | NH | 2-chloropyridin-5-yl | isopropyl | 3-phenoxybenzyl | oil |
| 24 | O | 2-methylbenzoxazol-5-yl | isopropyl | 3-phenoxybenzyl | oil |
| 25 | O | 2-methylbenzoxazol-6-yl | isopropyl | 3-phenoxybenzyl | oil |
| 26 | O | 2-n-butylbenzoxazol-6-yl | isopropyl | 3-phenoxybenzyl | oil |

TABLE I-continued

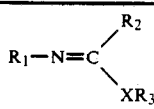

| Cmpd. No. | X | R₁ | R₂ | R₃ | Physical Constant |
|---|---|---|---|---|---|
| 27 | O | 2-isopropyl-benzoxazol-6-yl ((CH₃)₂CH-) | isopropyl | 3-phenoxybenzyl | oil |
| 28 | O | 2-phenyl-benzoxazol-6-yl | isopropyl | 3-phenoxybenzyl | oil |
| 29 | S | 6-chloropyridin-3-yl | isopropyl | —CH₂-(3-(4-fluorophenoxy)phenyl) | oil |
| 30 | O | 6-chloropyridin-3-yl | isopropyl | —CH₂-(3-(4-chlorophenoxy)phenyl) | oil |
| 31 | O | 6-chloropyridin-3-yl | isopropyl | —CH₂-(2-fluoro-3-(4-fluorophenoxy)phenyl) | oil |
| 32 | O | 6-chloropyridin-3-yl | isopropyl | —CH₂-(2-fluoro-3-(4-chlorophenoxy)phenyl) | oil |
| 33 | O | 5-CF₃-pyridin-3-yl | isopropyl | 3-phenoxybenzyl | oil |
| 34 | O | 4-CF₃-pyridin-2-yl | isopropyl | 3-phenoxybenzyl | oil |
| 35 | O | 5-CF₃-pyridin-3-yl | isopropyl | —CH₂-(3-(4-fluorophenoxy)phenyl) | oil |
| 36 | O | 4-CF₃-pyridin-2-yl | isopropyl | —CH₂-(3-(4-fluorophenoxy)phenyl) | oil |
| 37 | O | 4-CF₃-pyridin-3-yl | isopropyl | —CH₂-(2-fluoro-3-(4-chlorophenoxy)phenyl) | oil |

TABLE I-continued $$R_1-N=C{\overset{R_2}{\underset{XR_3}{}}}$$

| Cmpd. No. | X | R₁ | R₂ | R₃ | Physical Constant |
|---|---|---|---|---|---|
| 38 | O | 2-(CH₃S)-pyridin-5-yl | isopropyl | 3-phenoxybenzyl | oil |
| 39 | O | 2-(CF₃CH₂O)-pyridin-5-yl | isopropyl | —CH₂-(3-(4-chlorophenoxy)phenyl) | oil |
| 40 | O | 2-(CF₃CH₂O)-pyridin-5-yl | isopropyl | 3-phenoxybenzyl | |
| 41 | O | 2-(C₂H₅O)-pyridin-5-yl | isopropyl | 3-phenoxybenzyl | oil |
| 42 | O | 2-(CF₃CH₂O)-pyridin-5-yl | isopropyl | —CH₂-(4-fluoro-3-phenoxyphenyl) | oil |
| 43 | O | 2-(CF₃CH₂O)-pyridin-5-yl | isopropyl | —CH₂-(3-(4-fluorophenoxy)phenyl) | oil |
| 44 | O | 2-(CF₃CH₂O)-pyridin-5-yl | isopropyl | —CH₂-(4-fluoro-3-(4-chlorophenoxy)phenyl) | oil |
| 45 | O | 2-(CF₃CH₂O)-pyridin-5-yl | isopropyl | —CH₂-(6-phenoxypyridin-2-yl) | oil |
| 46 | O | 2-(CF₃CH₂O)-pyridin-5-yl | isopropyl | —CH₂-(6-(4-chlorophenoxy)pyridin-2-yl) | oil |
| 47 | O | 2-Cl-pyridin-5-yl | —C(CH₃)=CH₂ | 3-phenoxybenzyl | oil |
| 48 | O | 2-Cl-pyridin-5-yl | —C(CH₃)=CH₂ | —CH₂-(4-fluoro-3-(4-chlorophenoxy)phenyl) | oil |

TABLE I-continued $$R_1-N=C\begin{subarray}{l}R_2\\XR_3\end{subarray}$$

| Cmpd. No. | X | $R_1$ | $R_2$ | $R_3$ | Physical Constant |
|---|---|---|---|---|---|
| 49 | O | (5-chloropyridin-2-yl) | $-C(CH_3)=CH_2$ | $-CH_2-$(2-fluoro-phenyl with phenoxy) | oil |

Insecticidal Evaluation Tests

The compounds in Table I above were tested for insecticidal activity using the following testing procedures. $LC_{50}$ values, based on the results of these tests and calculated according to dosage-mortality curves, are expressed in Table II.

Housefly Musca domestica

The test compound was diluted in acetone and aliquots pipetted onto the bottom of aluminum dishes. To ensure even spreading of the chemical on the bottom of the dishes, 1 ml of acetone containing 0.01% peanut oil was also added to each dish. After all solvents had evaporated, the dishes were placed in circular cardboard cages containing 25 female houseflies, 1–2 days old. The cages were covered on the bottom with cellophane and on the top with tulle netting, and each contained a sugar-water saturated cotton plug for maintenance of the flies. Mortality was recorded after 48 hours. Test levels ranged from 100 µg/25 female houseflies downward. The LC-50 value is expressed below in Table II under the heading "HF", in terms of µg of the test compound per 25 female flies.

Black Bean Aphid Aphis fabae (Scop.)

Nasturtium plants (Tropaeolum sp.) approximately 5 cm tall, were transplanted into sandy loam soil in small cups and infested with 25–50 black bean aphids of mixed ages. Twenty-four hours later they were sprayed to the point of runoff with 50—50 acetone-water solutions of the test compound. Treated plants were held in the greenhouse and mortality was recorded after 48 hours. Test concentrations ranged from 0.05% downward. The LC-50 value is expressed below in Table II under the heading "BA" in terms of percent of the test compound in the sprayed solution.

Tobacco Budworm Heliothis virescens (Fabricius)

Eggs: Paper towel patches of 2-day old eggs of the tobacco budworm were dipped in acetone solutions of the test compound and placed in petri dishes containing a portion of larval rearing medium. Treated eggs were maintained at 78° F. and mortality was recorded after all control eggs had hatched and the young larvae were feeding on the media. Test concentrations ranged from 0.1% downward. The LC-50 value is expressed below in Table II under the heading "TBW-E" in terms of percent of the test compound in the solution.

Cabbage Looper Trichoplusia ni (Hübner)

The test compound was diluted in a 50—50 acetone-water solution Cotyledons of hyzini squash (Calabacita abobrinha), approximately 1×1.5 inches, were immersed in the test solutions for 2-3 seconds and placed on a wire screen to dry. The dried leaves were placed in petri dishes containing a moistened piece of filter paper and infested with 5 secondinstar cabbage looper larvae. The dishes were placed in a high humidity chamber. Mortality of the larvae was recorded 3-5 days later. Test concentrations ranged from 0.1% downward. The LC-50 value is expressed below in Table II under the heading "CL" in terms of percent of the test compound in solution.

Western Spotted Cucumber Beetle Larvae Diabrotica undecimpunctata undecimpunctata (Mannherheim)

Ten grams of moist potting soil was placed in a plastic cup. The test compound was dissolved in acetone. A 0.05 ml aliquot of the test sample, diluted to the desired concentration, was added to the soil. The cup was capped and the soil was mixed on a vortex mixer for approximately 15 seconds. An indentation was made on the surface of the soil and approximately 50 Diabrotica eggs were added. The eggs were covered with soil and maintained at room temperature (approximately 70° F. or 21° C.). Four days later a section of Romaine lettuce (Latuca sativa) leaf was placed in the treated cups. One week later the cups were examined for live larvae. Test concentrations ranged from 25 ppm downward. The LC-50 value is expressed below in Table II under the heading "Diabrotica" in terms of ppm of the test compound in the soil.

Acaricidal Evaluation Test

The two-spotted mite (2SM) [Tetranychus urticae (Koch)] was employed in tests for miticides. The test procedure was as follows:

Pinto bean plants (Phaseolus sp.) approximately 10 cm tall, were transplanted into sandy loam soil in small cups and thoroughly infested with two-spotted mites of mixed ages and sexes. Twenty-four hours later the infested plants were inverted and dipped for 2-3 seconds in 50—50 acetone-water solutions of the test compound. Treated plants were held in the greenhouse, and 5-7 days later mortality was determined for both adult mites and the nymphs hatching from eggs which were on the plants at the time of treatment. Test concentrations ranged from 0.05% downward. The LC-50 value is expressed below in Table II under the headings "2SM-A" (i.e., adults) and "2SM-E" (i.e. eggs) in terms of percent concentration of the test compound in the solution.

The results of these tests are shown in Table II.

TABLE II

| Cmpd. No. | HF μg | BA % | (LC₅₀) 2-SM A/% | (LC₅₀) 2-SM E/% | TBW E/% | CL, % | Diabrotica, ppm (soil) |
|---|---|---|---|---|---|---|---|
| 1 | 5.5 | 0.001 | >0.05 | >0.05 | 0.04 | 0.005 | >25 |
| 2 | 18 | 0.003 | >0.05 | >0.05 | 0.075 | 0.0027 | >25 |
| 3 | 7 | 0.003 | >0.05 | >0.05 | >0.1 | 0.0075 | >25 |
| 4 | 42 | 0.05 | >0.05 | >0.05 | >0.1 | 0.008 | >25 |
| 5 | 8 | 0.003 | >0.05 | >0.05 | 0.09 | 0.008 | >25 |
| 6 | >100 | >0.05 | >0.05 | >0.05 | >0.1 | 0.004 | >25 |
| 7 | >100 | >0.05 | >0.05 | >0.05 | >0.1 | 0.022 | >25 |
| 8 | >100 | >0.05 | >0.05 | >0.05 | >0.1 | 0.1 | >25 |
| 9 | >100 | >0.05 | >0.05 | >0.05 | >0.1 | 0.035 | >25 |
| 10 | 25 | 0.05 | >0.05 | >0.05 | >0.1 | >0.1 | — |
| 11 | 7 | 0.01 | >0.05 | >0.05 | >0.1 | 0.01 | — |
| 12 | 12 | 0.05 | >0.05 | >0.05 | >0.1 | 0.02 | — |
| 13 | 7 | >0.05 | — | — | >0.1 | 0.015 | — |
| 14 | >100 | >0.05 | >0.05 | >0.05 | >0.1 | 0.01 | >25 |
| 15 | 58 | >0.05 | >0.05 | >0.05 | >0.1 | 0.05 | >25 |
| 16 | 59 | — | >0.05 | >0.05 | >0.1 | 0.025 | >25 |
| 17 | 36 | — | >0.05 | >0.05 | >0.1 | 0.05 | >25 |
| 18 | 8 | — | >0.05 | >0.05 | >0.1 | 0.009 | >25 |
| 19 | 10 | — | >0.05 | >0.05 | >0.1 | 0.04 | >25 |
| 20 | 6 | — | — | — | — | 0.009 | — |
| 21 | >100 | — | >0.05 | >0.05 | >0.1 | 0.05 | >25 |
| 22 | 9 | — | >0.05 | >0.05 | 0.05 | 0.001 | >25 |
| 23 | >100 | — | >0.05 | >0.05 | >0.1 | 0.1 | >25 |
| 24 | >100 | — | >0.05 | >0.05 | >0.1 | 0.0075 | >25 |
| 25 | 38 | — | >0.05 | >0.05 | >0.1 | 0.0075 | >25 |
| 26 | >100 | 0.05 | >0.05 | >0.05 | >0.1 | 0.004 | — |
| 27 | >100 | >0.05 | >0.05 | >0.05 | >0.1 | 0.0035 | — |
| 28 | >100 | >0.05 | >0.05 | >0.05 | >0.1 | 0.04 | >25 |
| 29 | >100 | >0.05 | >0.05 | >0.05 | >0.1 | 0.025 | >25 |
| 30 | 15 | >0.05 | >0.05 | >0.05 | 0.1 | 0.0007 | >25 |
| 31 | 7.5 | — | >0.05 | >0.05 | 0.45 | 0.0016 | >25 |
| 32 | 22 | — | >0.05 | 0.05 | 0.03 | 0.00075 | >25 |
| 33 | 5 | >0.05 | >0.05 | >0.05 | 0.075 | 0.0035 | >25 |
| 34 | >100 | — | >0.05 | >0.05 | >0.1 | 0.018 | >25 |
| 35 | 23 | — | >0.05 | >0.05 | 0.1 | 0.001 | >25 |
| 36 | >100 | — | >0.05 | >0.05 | >0.1 | 0.015 | >25 |
| 37 | 40 | >0.05 | >0.05 | >0.05 | >0.1 | >0.1 | >25 |
| 38 | <100 | 0.005 | >0.05 | >0.05 | >0.1 | >0.1 | >25 |
| 39 | >100 | 0.001 | 0.006 | 0.006 | 0.02 | >0.1 | >25 |
| 40 | <100 | 0.0003 | 0.006 | 0.006 | 0.045 | 0.00029 | >25 |
| 41 | <100 | >0.05 | >0.05 | >0.05 | >0.1 | 0.0014 | >25 |
| 42 | <100 | 0.0004 | 0.006 | 0.006 | 0.017 | 0.000075 | >25 |
| 43 | >100 | 0.0003 | 0.006 | 0.006 | 0.02 | 0.00015 | >25 |
| 44 | >100 | 0.0003 | 0.001 | 0.001 | 0.01 | 0.00017 | >25 |
| 45 | <100 | 0.001 | 0.03 | 0.03 | >0.1 | 0.00075 | >25 |
| 46 | <100 | 0.0003 | 0.006 | 0.006 | 0.017 | 0.00027 | >25 |
| 47 | <100 | 0.05 | >0.05 | >0.05 | <0.1 | <0.1 | >25 |
| 48 | <100 | <0.05 | >0.05 | >0.05 | <0.1 | <0.1 | >25 |
| 49 | <100 | <0.05 | >0.05 | >0.05 | 0.1 | <0.1 | >25 |

Key:
C = Contact Test
E = Test on eggs
A = Test on Adults

Some compounds of this invention were also evaluated against other insects, including aster leafhopper (*Macoosteles fascifrens* [Stal]) and maize weevil (*Sibophilus zeamais* [Motschulsky]). With a few exceptions, the tested compounds did not produce 50% or greater activity at the levels tested.

The insecticidal activity of compounds defined by Formula (I) may be determined by evaluating such a compound using one or more of the above-described procedures. Compounds demonstrating activity against one or more of such insects are considered "insecticidal" for the purposes of this invention.

In practice, a pure compound (active compound) can be used as an insecticide. However, in general, the compounds are first formulated with one or more inert (i.e. non-chemically reactive, plant compatible or herbicidally inert) carriers or diluents suitable for insecticidal use, before being applied.

The compositions or formulations, including a compound (I) as described herein, may take any one of a number of solid or liquid forms. Examples of solid forms are dusts, granules, tablets, powders and the like. Examples of liquid forms are emulsions, solutions, suspensions, flowables, emulsifiable concentrates and pastes. Such compositions may contain, in addition to the active compound or compounds, various carriers or diluents; surface-active agents (wetting agents, dispersing agents and/or emulsifying agents); solvents (water, or organic solvents such as aromatic solvents or chlorinated aliphatic solvents); adhesives; thickeners; binders; anti-foaming agents; and other substances as mentioned herein. Solid carriers or diluents included in such compositions or formulations may include, for example, ground natural minerals such as kaolins, alumina, calcined diatomaceous earth, calcium carbonate, silica, kieselguhr, clays, etc.; ground synthetic minerals such as various silicates and alumino-silicates and ground vegetable products such as bark, cornmeal, sawdust, cellulose powder and the like. Compositions containing sorptive clays will usually also contain a stabilizer, such as a glycol, to prevent or minimize degradation of the active ingredient.

To manufacture solid compositions, the active compounds are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Wettable powders and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents may also be added.

Flowables are prepared by mixing an active compound with one or more dispersing agents and/or solid additives, and a liquid (which may be water or an organic solvent) in which the active compound is relatively insoluble, and grinding the mixture.

Both liquid and solid compositions may be in microcapsule or encapsulated form, to permit release of the enclosed active compound at a controlled rate over a period of time. Liquid compositions of this type contain encapsulated droplets of approximately 1-50 microns in diameter, including the active compound and optionally a solvent. The encapsulating material is an inert porous membrane of a polymeric material.

Solid encapsulated compositions generally take the form of granules, in which the liquid containing the active component is trapped in the pores of the granular support by a porous polymeric membrane through which the active ingredient may migrate at a controlled rate, or which membrane breaks down at a controlled rate to permit escape of the active ingredient.

Typical encapsulating materials include natural and synthetic rubbers, cellulosic materials, styrene-butadiene copolymers, polyacrylonitriles, polyacrylates, polyamides, polyisocyanates, polyurethanes, mixed copolymers of the foregoing and starch xanthates.

It is possible to use highly concentrated liquid compositions containing up to about 95% by weight of the active compound, or even the 100% active compound alone, when applying the compound in the form of a finely divided liquid by use of various atomizing equipment, for example by airplane spraying techniques. For other purposes, however, the various types of compositions which can be utilized for these compounds will contain varying amounts of the compound according to the type of composition and the intended use.

In general, insecticidal compositions may contain from 5 to 95% of the active compound, more preferably from 10 to 85%. Some typical compositions will contain an active compound as follows: wettable powders: 25 to 80% active compound: oil suspensions, emulsions, solutions, flowables, and emulsifiable concentrates: 5 to 85% active compound: aqueous suspensions: 20 to 50% active compound; dusts and powders: 5 to 20% active compound; granules and pellets: 5 to 20% active compound.

In addition to the active compound and the various agents utilized in preparing compositions and formulations mentioned, such compositions may also contain one or more other active compounds of the type mentioned herein as well as other active pesticidal agents, such as herbicides, fungicides, insecticides, acaricides, nematocides, bactericides, and plant growth regulators. The particular pesticide included in the mixture will depend upon its intended utility and the type of complementary action required. Examples of suitable insecticides include the following:

(a) natural pyrethrins or pyrethroids such as permethrin, esfenvalerate, deltamethrin, cyhalothrin, biphenthrin, fenpropathrin, cyfluthrin, tefluthrin, empenthrin, ethofenprox, natural pyrethrins, tetramethrin, bioallethrin, fenfluthrin, prallethrin, 5benzyl- 3-furylmethyl-(E)-(1R,3S)-2,2-dimethyl-3-(2-oxothiolan-3-ylidenemethyl)-cyclopropane carboxylate, and pentafluorobenzyl(cis)-3-[2-fluoro-2-(methoxycarbonyl)ethenyl]-2,2-dimethyl-cyclopropane carboxylate.

(b) organophosphates such as profenofos, sulprofos, phosmet, dichlorvos, methyl parathion, azinphos-methyl, dimeton-s-methyl, heptenophos, thiometon, fenamiphos, monocrotophos, profenophos, triazophos, methamidophos, dimethoate, phosphamidon, malathion, chlorpyrifos, phosalone, fensulfothion, fonofos, phorate, phoxim, pyrimihos-methyl, fenitrothion and diazinon;

(c) carbamates (including aryl carbamates) such as pirimicarb, cloethocarb, carbofuran, ethiofencarb, aldicarb, thiofurox, carbosulfan, bendiocarb, fenobucarb, propoxur and oxamyl;

(d) benzoyl ureas such as triflumuron, chlorofluazuron;

(e) organic tin compounds such as cyhexatin, fenbutatin oxide, and azocyclotin;

(f) macrolides such as avermectins or milbemycins, for example such as abamectin, avermectin, and milbemycin;

(g) hormones and synthetic mimics thereof such as juvenile hormone, juvabione, ecdysones, methoprene and hydroprene;

(h) pheromones; and (i) organochlorine compounds such as benzene hexachloride, DDT, chlordane or dieldrin.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofesin, can be employed. Alternatively, insecticides specific for particular insect species/stages, for example ovolarvicides such as clofentezine, amitraz, chlordimeform flubenzimine, hexythiazox and tetradifon, motilicides such as dicofol or propargite, adulticides such as bromopropylate, chlorobenzilate, or insect growth regulators such as hydramethylon, cyromazine, methoprene, chlorofluazuron and diflubenzuron may also be included in the compositions. Such compositions may also contain soil disinfectants or fumigants and may further contain fertilizers, thus making it possible to provide multi-purpose compositions containing one or more of the active compounds described herein as well as, optionally, other pesticides and also fertilizers, all intended and formulated for use at the same locus.

Control of insect pests is accomplished by applying a composition containing an insecticidally effective amount of an active compound as described herein to the insect, to a locus at which insecticidal control is desired, or to food sources (including seeds) on which the insects feed. For use in the last mentioned manner it is preferable to utilize a compound which is not volatile. Thus, control may be achieved by direct application of the active compounds to the insects and indirectly by application of the compounds to a locus to be protected (such as crop lands, grass ranges and forests), to a source of food for insects or to other insect habitats (for example, breeding or swarming areas). The rates of application of the active compound, and the concentration applied, will vary according to whether the compound or composition is being directly applied to the insect or indirectly, to a locus, food or habitat. In the latter case the rate of the application, depending on the nature of the insect or insects to be controlled, and the plant environment, will generally vary from about 0.01 to about 100 pounds per acre (about 0.011 to about 111 kg/ha).

It should be noted that the active compound need not be insecticidally active per se to effect insect control. The purposes of this invention are fully served if such compounds are rendered active by external influences, such as light or heat, or by some physiological action which occurs when the compound is ingested into the body of the insect.

Compounds of this invention could be used to control a variety of insects such as:
*Myzus persicae* (aphid)
*Aphis gossypii* (aphid)
*Aphis fabae* (aphid)
*Megoura viceae* (aphid)
*Aedes aegypti* (mosquito)
Anopheles spp. (mosquitos)
Culex spp. (mosquitos)
*(Dysdercus fasciatus* (capsid)
*Musca domestica* (housefly)
*Pieris brassicae* (white butterfly)
*Plutella maculipennis* (diamond back moth)
*Phaedon cochlaeriae* (mustard beetle)
Aonidiella spp. (scale insects)
Trialeuroides spp. (white flies)
*Bemisia tabaci* (white fly)
*Blatella germanica* (cockroach)
*Periplaneta americana* (cockroach)
*Blatta orientalis* (cockroach)
*Spodoptera littoralis* (cotton leafworm)
*Heliothios virescens* (tobacco budworm)
*Chorticocetes terminifera* (locust)
Diabrotica spp. (rootworms)
Agrotis spp. (cutworms)
*Chilo suppressalis* (stem borer)
*Chilo partellus* (maize stem borer)
*Nilaparvata lugens* (plantopper)
*Nephottex virescens* (leafhopper)
*Nephotettix cincticeps* (leafhopper)
*Panonychus ulmi* (European red mite)
*Panonychus citri* (citrus red mite)
*Tetranychus urticae* (two-spotted spider mite)
*Tetranychus cinnabarinus* (carmine spider mite)
*Phyllcoptruta oleivora* (citrus rust mite)
*Polyphagotarsonemus latus* (broad mite)
Brevipalpus spp. (mites)

Compositions containing one or more of the active compounds described, in an insecticidally effective amount, may be applied to the plant, locus or insect habitat in any conventional manner.

When used in connection with crop or other plant protection, application may be made in a preventive (i.e. before infestation) or eradicative manner (i.e., after infestation). Thus, powders and various liquid compositions containing the active compound can be applied by the use of mower dusters, boom and hand sprayers and spray dusters, or applied from airplanes as dusts or sprays. When applied in the latter method they may be effective in very low dosages.

Compositions including active compounds may also be applied by addition to irrigation waters supplied to the field to be treated. This method of application permits penetration of the compounds into the soil as the water is absorbed therein.

Compositions including active compounds may additionally be used to protect plant seeds from being attacked by soil-borne insect pests after planting and during germination, by applying the composition to the seeds as a seed dressing. This is performed generally by mixing the seeds with an active composition in either liquid or solid form (preferably liquid) in a suitable mixing apparatus. Liquid compositions for this purpose may contain an adhesive or sticking agent, such as methyl cellulose, ethyl cellulose, etc., to assist the composition in adhering to the seed. If a solid composition is utilized for this purpose, an adhesive agent may be sprayed on the seeds during or after mixing.

For use as a soil insecticide, the active compound, or compositions containing it, may be mixed with the soil in any conventional manner, before, during or after planting of the plant seeds. Liquid compositions may be applied by spraying onto the surface or by incorporation in irrigation or sprayed water. Solid or liquid compositions containing an active compound may be incorporated into the soil prior to or during planting by discing, plowing or other mixing operations, or after planting as a side dressing, in order to locate the active ingredient below the surface of the soil so as to be most effective in controlling undesirable larvae.

Some examples of compositions containing the active compounds of this function are:

| Component | | Weight % |
| --- | --- | --- |
| Composition A: Granular Solid | | |
| Active compound | | 10 |
| attapulgite clay granules | | 85 |
| triethylene glycol | | 5 |
| | Total | 100% |
| Composition B: Wettable Powder | | |
| Active compound | | 80 |
| wetting agent (sodium dialkyl-naphthalene sulfonate) | | 1 |
| dispersing agent (sodium lignosulfonate) | | 4 |
| diluent (aluminum magnesium silicate) | | 15 |
| | Total | 100% |
| Composition C: Dilute Solution | | |
| Active compound | | 5 |
| solvent (xylene) | | 95 |
| | Total | 100% |
| Composition D: Emulsifiable Concentrate | | |
| Active compound | | 50 |
| Emulsifier (blend of metal sulfonates and polyoxyethylene ethers) | | 10 |

| -continued | |
|---|---|
| Component | Weight % |
| solvent (xylene) | 40 |
| Total | 100% |
| Composition E: Concentrated Solution | |
| Active compound | 90 |
| solvent (xylene) | 10 |
| Total | 100% |

What is claimed is:

1. A compound having the formula $$R_1-N=C\begin{matrix}R_2\\XR_3\end{matrix}$$

wherein $R_1$ is pyridyl, optionally substituted by from 1 to 4 groups selected from halo, $C_1$-$C_6$ alkyl, $C_1$-$C_4$ haloalkyl, $C_1$-$C_4$ haloalkoxy, or $C_1$-$C_4$ alkylthio, provided that $R_1$ is not 3-chloro-5-trifluoromethylpyrid-2yl;

$R_2$ is methyl, ethyl, n-propyl, $C_3$-$C_7$ branched alkyl, $C_3$-$C_4$ cycloalkyl, $C_2$-$C_6$ alkenyl, $C_2$-$C_6$ haloalkenyl, $C_1$-$C_6$ haloalkyl, $C_2$-$C_6$ alkoxyalkyl or cyclopropyl substituted by up to four methyl groups or up to two halogens; X is oxygen, sulfur or —NH—; and when X is oxygen, then $R_3$ is:

$$-\overset{R_6}{\underset{}{CH}}-(CH_2)_m-\overset{A}{\underset{B}{\diagup}}\overset{R_7}{\underset{K}{\diagdown}}$$
$$\phantom{-CH-(CH_2)_m-}\overset{}{\underset{R_4}{\diagdown}}$$

in which m is 0 or 1;

A, B and K are each carbon or nitrogen, provided that no more than one of A, B, and K is nitrogen;

$R_4$ is hydrogen, monohalo or dihalo;

$R_6$ is hydrogen, methyl, fluoro or ethynyl; and $R_7$ is $$-O\overset{D}{\underset{E}{\diagup}}$$
$$\phantom{-O}\overset{}{\underset{R_5}{\diagdown}}$$

in which D and E are each carbon or nitrogen provided that both D and E are not nitrogen, and further provided that if A, B or K is nitrogen, then D and E are both carbon; and $R_5$ is hydrogen, $C_1$-$C_4$ alkyl, $C_1$-$C_4$ alkoxy, trifluoromethyl, cyano, $C_1$-$C_4$ alkylthio, $C_1$-$C_4$ alkylsulfonyl, or mono- or polyhalo;

(ii) $-NH-\!\!\!\bigcirc\!\!\!-R_8$ $-CH_2-\!\!\!\bigcirc\!\!\!-R_8$ $-OCH_2-\!\!\!\bigcirc\!\!\!-R_8$ in which $R_8$ is hydrogen or halogen; or (iii) —O—$CH_2$—CH=$CH_2$ (b) $-CH_2-\!\!\!\bigcirc\!\!\!\begin{matrix}R_9\\(R_{10})_4\end{matrix}$ in which (i) $R_9$ is 4-fluoro, 4-methoxymethyl, or 4-propargyl, and $R_{10}$ is fluoro or (ii) $R_9$ is 3- or 4-allyl, 3- or 4-propargyl, or 3- or 4-(mono- or dihalo)allyl, and $R_{10}$ is hydrogen or fluoro;

(c) $-CH_2-\!\!\!\underset{O}{\bigcirc}\!\!\!-CH_2-\!\!\!\bigcirc$;

(d) 4-phenoxy-2-butyn-2-yl;
(e) 4-(benzyloxy)benzyl;
(f) 4-(4-fluorobenzyloxy)benzyl; or (g) $-CH_2-\!\!\!\bigcirc\!\!\!\overset{CH_3}{\phantom{|}}\!\!\!-\!\!\!\bigcirc$ and if X is sulfur or —NH—, then $R_3$ is $$-\overset{R_{13}}{\underset{}{CH}}-(CH_2)_n-\!\!\!\overset{F}{\underset{R_{11}}{\diagup}}\!\!\!-O-\!\!\!\bigcirc\!\!\!-R_{12}$$

in which n is 0 or 1; F and G are independently nitrogen or carbon, provided that F and G are not both nitrogen; $R_{11}$ is hydrogen or halo; $R_{12}$ is hydrogen, mono- or dihalo, $C_1$-$C_4$ alkyl, $C_1$-$C_4$ alkoxy, trifluoromethyl, cyano, $C_1$-$C_4$ alkylthio, $C_1$-$C_4$ alkylsulfonyl; and $R_{13}$ is hydrogen or methyl; (j) pentafluorobenzyl; or (k) 2-methyl-3-phenylbenzyl.

2. A compound according to claim 2 in which $R_1$ is a mono- or disubstituted pyridyl group in which the substituents are halo, trifluoromethyl, methoxy, ethoxy, 2,2,2,-trifluoroethoxy, methylthio or methyl.

3. A compound according to claim 1 in which $R_3$ has the formula

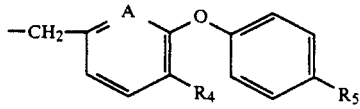

in which A is nitrogen or carbon and $R_4$ and $R_5$ are each independently hydrogen or halogen.

4. A compound according to claim 3 in which A is carbon, and $R_4$ and $R_5$ are both hydrogen.

5. A compound according to claim 3 in which A is carbon, $R_4$ is hydrogen and $R_5$ is halogen.

6. A compound according to claim 3 in which A is carbon, $R_4$ is halogen and $R_5$ is hydrogen.

7. A compound according to claim 3 in which A is carbon and $R_4$ and $R_5$ are both halogen.

8. A compound according to claim 7 in which $R_4$ is fluoro and $R_5$ is chloro.

9. A compound according to claim 1 wherein X is oxygen.

10. A compound according to claim 9 wherein $R_3$ is 3-phenoxy-benzyl.

11. A compound according to claim 10 wherein $R_2$ is isopropyl.

12. The compound according to claim 11 wherein $R_1$ is 6-chloro-3-pyridyl.

13. The compound according to claim 11 wherein $R_1$ is 2,6-dichloro 3-pyridyl.

14. The compound according to claim 11 wherein $R_1$ is 6-methoxy-3- pyridyl.

15. The compound according to claim 11 wherein $R_1$ is 5-trifluoromethyl-2-pyridyl.

16. The compound according to claim 11 wherein $R_1$ is 6-fluoro-3-pyridyl.

17. The compound according to claim 11 wherein $R_1$ is 2,3,5,6-tetrafluoro-4-pyridyl.

18. The compound according to claim 11 wherein $R_1$ is 6-methyl-3-pyridyl.

19. The compound according to claim 11 wherein $R_1$ is 6-bromo-3-pyridyl.

20. The compound according to claim 11 wherein $R_1$ is 5-bromo-3-pyridyl.

21. A compound according to claim 12 wherein $R_1$ is 4-(2,2,2-trifluoroethoxy)-3-pyridyl.

22. A compound according to claim 10 wherein $R_2$ is cyclopropyl.

23. The compound according to claim 22 wherein $R_1$ is 6-chloro-3-pyridyl.

24. The compound according to claim 22 wherein $R_1$ is 6-methoxy-3-pyridyl.

25. A compound according to claim 10 wherein $R_2$ is 2-(2-chloropropyl).

26. The compound according to claim 25 wherein $R_1$ is 6-bromo-3-pyridyl.

27. A compound according to claim 9 wherein $R_3$ is 3-(4-fluorophenoxy)benzyl.

28. A compound according to claim 27 wherein $R_1$ is 6-chloro-3-pyridyl and $R_2$ is isopropyl.

29. The compound according to claim 1 wherein $R_1$ is 4-chloro-3-pyridyl, $R_2$ is isopropyl, $R_3$ is 3-(4-chlorophenoxy)benzyl and X is oxygen.

30. The compound according to claim 1 wherein $R_1$ is 4-(2,2,2-trifluoroethoxy)-3-pyridyl, $R_2$ is isopropyl, $R_3$ is 3-(4-fluorophenoxy)benzyl and X is oxygen.

31. The compound according to claim 1 wherein $R_1$ is 4-(2,2,2-trifluoroethoxy)-3-pyridyl, $R_2$ is isopropyl, $R_3$ is 3-(4-chlorophenoxy)-4-fluorobenzyl and X is oxygen.

32. The compound according to claim 1 in which $R_1$ is 4-(2,2,2-trifluoroethoxy)-3-pyridyl, $R_2$ is isopropyl, $R_3$ is 3-phenoxy-pyrid-2-ylethyl and X is oxygen.

33. A compound according to claim 1 wherein $R_2$ is isopropenyl and X is oxygen.

34. A compound according to claim 1 in which $R_1$ is 6-chloro-3-pyridyl, $R_2$ is isopropyl, $R_3$ is 3-(4-fluorphenoxy)benzyl and X is sulfur.

35. A method for controlling insects comprising applying to an insect, the locus of an insect or a locus at which insecticidal control is desired, an insecticidally effective amount of a compound according to claim 1.

36. An insecticidal composition comprising (a) an insecticidally effective amount of a compound according to claim 1; and (b) an insecticidally suitable diluent or carrier.

37. A compound according to claim 2 in which $R_2$ is isopropyl, cyclopropyl or isopropenyl.

38. A compound according to claim 2 in which $R_3$ has the formula

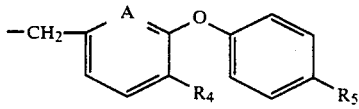

in which A is nitrogen or carbon and $R_4$ and $R_5$ are each independently hydrogen or halogen.

39. A compound according to claim 38 in which A is carbon and $R_4$ and $R_5$ are both hydrogen.

40. A compound according to claim 38 in which A is carbon, $R_4$ is hydrogen and $R_5$ is halogen.

41. A compound according to claim 38 in which A is carbon and $R_4$ and $R_5$ are both halogen.

42. A compound according to claim 41 in which $R_4$ is fluoro and $R_5$ is chloro.

43. A compound according to claim 41 in which $R_4$ and $R_5$ are both fluoro.

44. A compound according to claim 38 in which X is oxygen.

45. A compound according to claim 44 in which $R_3$ is 3-phenoxybenzyl.

* * * * *

UNITED STATES PATENT AND TRADEMARK OFFICE
CERTIFICATE OF CORRECTION

PATENT NO. : 4,994,473
DATED : February 19, 1991
INVENTOR(S) : Michael D. Broadhurst It is certified that error appears in the above-identified patent and that said Letters Patent is hereby corrected as shown below:

In Column 27, line 34 should read --- (a) --- preceding the formula.

In Column 27, line 47 should read --- (i) --- preceding the formula.

In Column 28, line 14, a semicolon should follow --- $O-CH_2-CH=CH_2$ ---.

In Column 28, line 47 should read --- (h) --- preceding the formula.

In Column 28, line 63, "claim 2" should read --- claim 1 ---.

Signed and Sealed this

Twelfth Day of April, 1994

Attest:

BRUCE LEHMAN

*Attesting Officer*    *Commissioner of Patents and Trademarks*